US00PP19550P3

(12) United States Plant Patent
Kools

(10) Patent No.: US PP19,550 P3
(45) Date of Patent: Dec. 9, 2008

(54) BLUE SPRUCE TREE NAMED 'BLUE DIAMOND'

(50) Latin Name: *Picea pungens*
Varietal Denomination: Blue Diamond

(75) Inventor: Nelis Kools, Deurne (NL)

(73) Assignee: Gebr. Van Vliet Boomkwekerijen B.V., Boskoop (NL)

( * ) Notice: Subject to any disclaimer, the term of this patent is extended or adjusted under 35 U.S.C. 154(b) by 0 days.

(21) Appl. No.: 11/725,425

(22) Filed: Mar. 19, 2007

(65) Prior Publication Data

US 2008/0235833 P1 Sep. 25, 2008

(51) Int. Cl.
*A01H 7/00* (2006.01)

(52) U.S. Cl. ..... Plt./213

(58) Field of Classification Search ..... Plt./213
See application file for complete search history.

(56) References Cited

PUBLICATIONS

UPOV–ROM GTITM Plant Variety Database, May 2007, GTI Jouve Retrieval Software, citation for blue spruce, 'Blue Diamond'.*

* cited by examiner

*Primary Examiner*—Annette H Para
*Assistant Examiner*—S. B. McCormick-Ewoldt
(74) *Attorney, Agent, or Firm*—Jondle & Associates, P.C.

(57) ABSTRACT

A blue spruce tree particularly distinguished by its strong, upright and pyramidal growth habit, propagation through cuttings rather than grafting and intense blue-colored foliage, is disclosed.

2 Drawing Sheets

Genus and species: *Picea pungens.*
Variety denomination: 'Blue Diamond'.

BACKGROUND OF THE NEW TREE

The present invention comprises a new and distinct variety of Blue Spruce, botanically known as *Picea pungens,* and hereinafter referred to by the cultivar name 'Blue Diamond'. The new variety originated in Deurne, The Netherlands in 1990 from a hybridization between the female parent, *Picea pungens* 'Glauca' (unpatented) and the male parent, an unknown *Picea pungens.*

The new variety was created in 1990 in Deurne, The Netherlands and has been asexually reproduced repeatedly by vegetative cuttings in Deurne, The Netherlands since 1991. The present invention has been found to retain its distinctive characteristics through successive asexual propagations.

Plant Breeder's Rights for this cultivar have been granted in the European Union on May 10, 2005.

SUMMARY OF THE INVENTION

The following are the most outstanding and distinguishing characteristics of the new variety when grown under normal horticultural practices in Deurne, The Netherlands.

1. Strong, upright and pyramidal growth habit;
2. Propagation from cuttings rather than grafting; and
3. Intense blue colored foliage.

DESCRIPTION OF THE PHOTOGRAPHS

This new blue spruce tree is illustrated by the accompanying photographs which show overall plant habit of the tree. The colors shown are as true as can be reasonably obtained by conventional photographic procedures. The plants were approximately 7 years old.

DESCRIPTION OF THE NEW TREE

Figure 1:
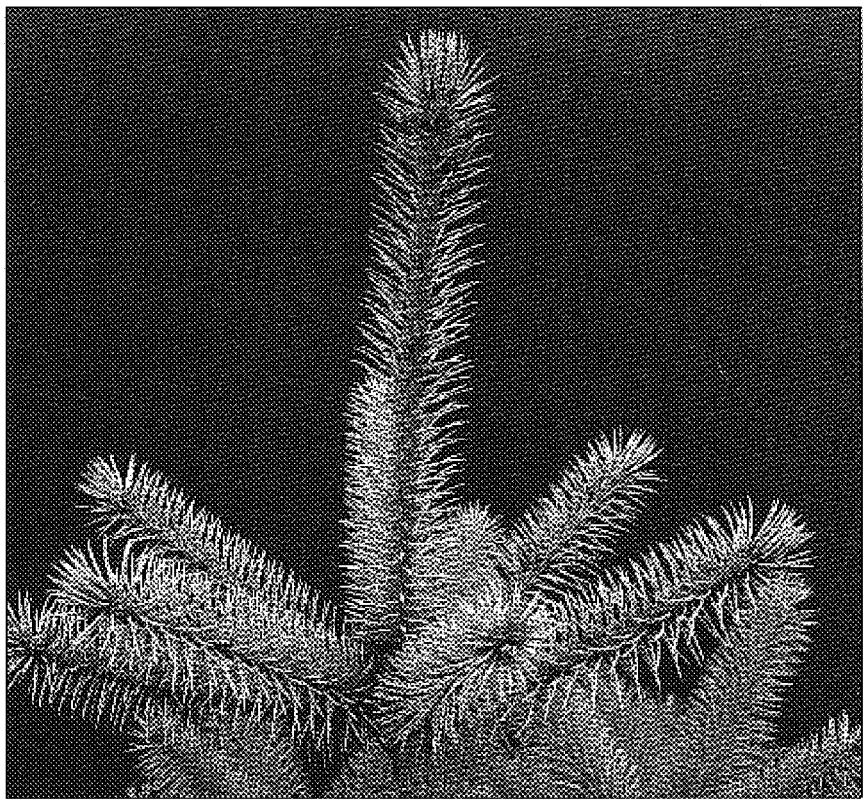
FIG. 1 shows a close-up of the upper part of the tree, the lateral branches and the needle-like leaves.
Figure 2:
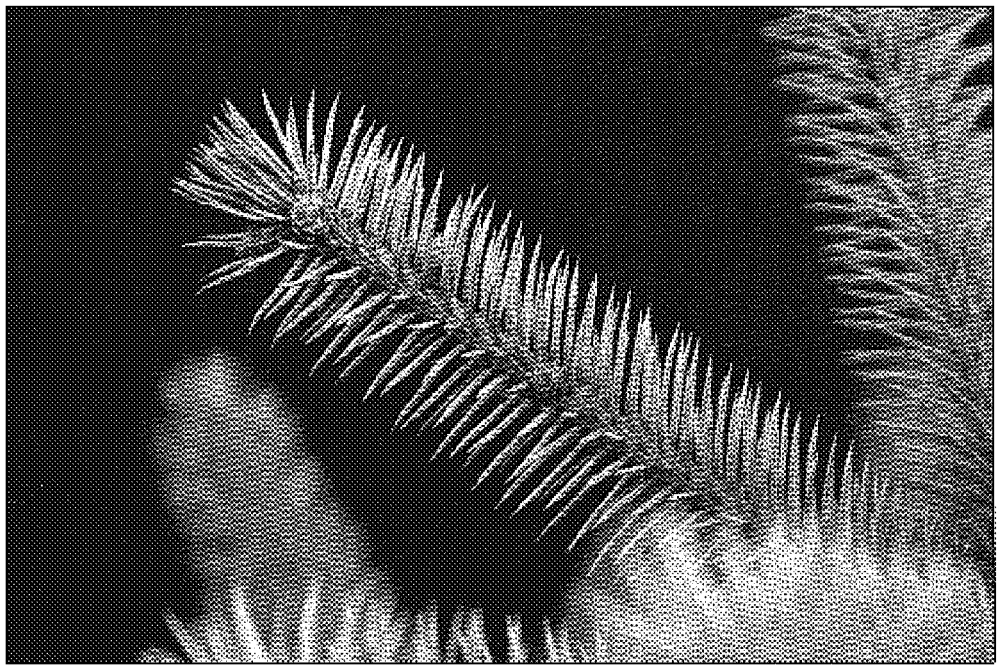
FIG. 2 shows a close-up of a lateral branch and the intense blue needle-like leaves.
Figure 3:
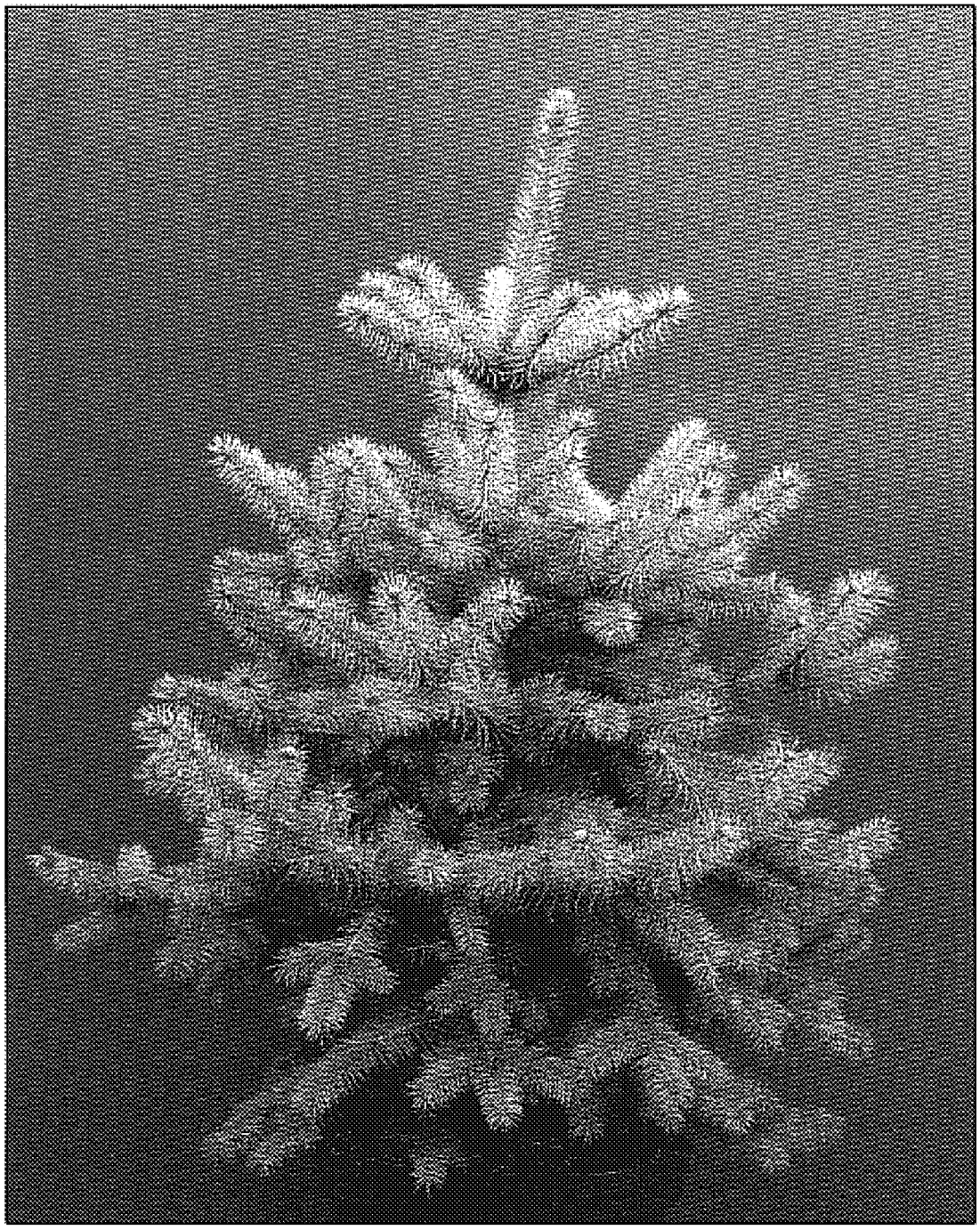
FIG. 3 shows the overall form of the tree.

The following detailed descriptions set forth the distinctive characteristics of 'Blue Diamond'. The data which define these characteristics were collected from asexual reproductions carried out in Deurne, The Netherlands. The plant history was taken in June from trees approximately 6-years old, grown outdoors in 12-liter containers in Boskoop, The Netherlands. Color readings were taken under natural light. Color references are primarily to the R.H.S. Colour Chart of The Royal Horticultural Society of London (R.H.S.) $4^{th}$ Edition.

DETAILED BOTANICAL DESCRIPTION

Classification:
- *Botanical.*—*Picea pungens.*
- *Common name.*—Blue Spruce.

Parentage:
- *Female parent.*—*Picea pungens* 'Glauca' (unpatented).
- *Male parent.*—An unknown *Picea pungens* (unpatented).

Growth:
- *Type.*—Shrub, evergreen conifer.
- *Shape/form.*—Conical/pyramidal.
- *Growth and branching habit.*—Upright, moderately vigorous; main stem (trunk) grows from base and has lateral branches.
- *Height.*—66.0 cm is reached in 6 years; 125 cm is reached in 12 years.

*Width* (*horizontal plant diameter*).—56.0 cm in 6 years; 90 cm in 12 years.
*Growth rate.*—15.0 cm per season.
*Diameter of trunk* (*at 0.4 meters above the ground*).—3.0 cm.
*Time to produce a finished plant.*—3 years with a height of 30 cm to 35 cm.
*Outdoor plant performance.*—Use in landscape beds.
*Range or average day temperatures.*—8° Celsius to 30° Celsius.
*Range or average night temperatures.*—2° Celsius to 15° Celsius but can easily withstand temperatures of minus 25° Celsius.

Leaves:
*Arrangement.*—Alternate, single.
*Quantity of leaves per lateral branch.*—650 needle-like leaves (excluding bi-lateral and tri-lateral branches).
*Shape.*—Needle-like, acicular.
*Apex.*—Acute.
*Base.*—Attenuate.
*Length.*—2.8 cm.
*Width.*—0.1 cm.
*Texture.*—Dull, smooth, covered with a waxy layer.
*Pubescence.*—Absent.
*Margin.*—Entire.
*Venation.*—Veins are not visible.
*Immature leaf.*—Color (for both upper and lower surfaces): RHS 122C and RHS 122D (Blue-green); when waxy layer is rubbed away, is RHS 144A (Yellow-green).
*Mature leaf.*—Color (for both upper and lower surfaces): RHS 122B (Blue-green); when waxy layer is rubbed away, is RHS 137A (Green).
*Durability to stress.*—Very high.
*Petioles.*—Absent, leaves are sessile.

Stems:
*Number of lateral branches per plant.*—33.
*Color.*—Young stems are RHS 145A (Yellow-green); older stems and bark are RHS 161A and RHS 161B (Greyed-yellow).
*Length.*—26.4 cm.
*Diameter.*—0.5 cm.
*Internode length.*—0.3 cm.
*Shape and appearance.*—Rounded, dull with a scale like appearance.
*Aspect.*—Rounded.
*Strength.*—Very Strong.
*Texture.*—Rough.

Fruit/seed set: No fruit or seed has been detected to date.
Disease and insect resistance: Disease and insect resistance is typical of the species.

COMPARISON WITH PARENTAL AND COMMERCIAL CULTIVARS

'Blue Diamond' differs from the female parent *Picea pungens* 'Glauca' in that 'Blue Diamond' has a regular pyramidal shape, while 'Glauca' has a less regular pyramidal shape. Additionally, 'Blue Diamond' has intense blue colored foliage and is grown from cuttings, while 'Glauca' has a foliage color that varies between green to blue and is grown from seed.

'Blue Diamond' differs from the male *Picea pungens* parent in that 'Blue Diamond' has a short, compact habit that reaches only 66 cm in height at 6 years and 125 cm in height at 12 years while a *Picea pungens* has a tall habit that reach up to 1,524 cm or 50 feet in height.

'Blue Diamond' differs from the commercial *Picea pungens* variety 'Hoopsi' (unpatented) in that 'Blue Diamond' is propagated from cuttings, while 'Hoopsi' is propagated through grafting. Additionally, 'Blue Diamond' has a natural pyramidal shape that requires little pruning, while 'Hoopsi' has a more open growth habit and requires greater pruning in order to maintain a pyramidal shape.

I claim:

1. A new and distinct cultivar of blue spruce tree as shown and described herein.

* * * * *